United States Patent [19]

Greenspan et al.

[11] Patent Number: 5,063,062
[45] Date of Patent: Nov. 5, 1991

[54] CLEANING COMPOSITIONS WITH ORANGE OIL

[75] Inventors: Douglas H. Greenspan, Louisville; Phillip A. Low, Littleton, both of Colo.

[73] Assignees: D. Greenspan; W. Ingram, both of Louisville, Calif.

[21] Appl. No.: 413,395

[22] Filed: Sep. 27, 1989

[51] Int. Cl.$^5$ .............................................. A61F 13/00
[52] U.S. Cl. .................................. 424/443; 424/195.1; 424/401; 252/142; 514/783; 514/846
[58] Field of Search ................. 424/443, 401; 514/783

[56] References Cited

U.S. PATENT DOCUMENTS

| | | | |
|---|---|---|---|
| 4,014,995 | 3/1977 | Juliano et al. | 514/783 |
| 4,533,487 | 8/1985 | Jones | 252/173 |
| 4,620,937 | 11/1986 | Dellutri | 252/162 |

OTHER PUBLICATIONS

D. Limonene as a Degreasing Agent Richard L. Coleman, The Citrus Industry, vol. 56, No. 11, Nov., 1975, pp. 23-25.

*Primary Examiner*—Thurman K. Page
*Assistant Examiner*—James M. Spear
*Attorney, Agent, or Firm*—Timothy J. Martin

[57] ABSTRACT

A cleaning composition for cleaning the skin contains orange oil, a pharmaceutically acceptable moisturizer and an emulsifying agent, Preferably the orange oil accounts for between 5% and 60% by volume, and it further preferred that the composition contains 40% orange oil by volume. The moisturizer is either glycerin, aloe vera, jojoba oil, safflower oil or a combination thereof. The emulsifying agent preferably is oatmeal. The composition is constituted to have a pH of between 4.5 and 6.0, and the composition may be packaged as moistened towellets in hermetic packets.

12 Claims, No Drawings

CLEANING COMPOSITIONS WITH ORANGE OIL

FIELD OF THE INVENTION

The present invention generally relates to cleaning compositions suitable for external application to human skin tissue in order to remove unwanted substances such as tar, caulking compounds, sealants, adhesives and the like. More specifically, however, the present invention is directed to a natural cleaning composition that utilizes only plant based ingredients. As such, the present invention is particularly adapted for cleaning non-water soluble products from the human skin in a safe, effective manner.

BACKGROUND OF THE INVENTION

A wide variety of cleaning compositions are known for external application to skin tissue in order to remove dirt and unwanted materials. Among these cleaning compounds are the various hard and liquid soaps which may be used for cleaning human skin, especially the hands. However, numerous substances with which the hands may be soiled do not respond to ordinary soap compositions. Examples of substances that are difficult to remove include grease, tar, oils, ink, caulking materials, adhesives, sealants, gums, cosmetics and other non-water soluble products.

While some cleaning compositions have been developed for these materials, the typical cleaners are harsh and can damage the skin, especially after prolonged use. Examples of these compounds include turpentine, acetone, toluene and other petroleum based products as well as ammonia based products. These products, though, often damage the skin and otherwise exhibit a high level of toxicity. Further, if inhaled during use, these petroleum based products may cause respiratory damage. When absorbed through the skin, the petroleum based products can cause damage to the major organs of the body and can have a less serious side effect of drying and chaffing the skin where applied. Thus, it should be appreciated that, although petroleum is a naturally occurring product, it is not toxilogically healthy for the human body. Accordingly, there have been substantial efforts which have been made to find suitable alternative substances for skin cleaning. While some synthetically derived substances have been developed, many of these substances are medically suspect, and in some instances produce side effects making them unsuitable for use on a regular basis.

Orange oil, as a natural product derived from the rind of oranges, has been recognized in the past to have some cleaning capabilities. Prior to the present invention, however, it is not believed that the suitability of orange oil in cleaning human skin was realized. Orange oil by itself is a skin irritant that can cause inflammation of the tissues. When used by itself, fumes from orange oil may cause headaches, dizziness and other side effects. Accordingly, it has not been readily apparent that orange oil alone or in combination with other substances could prove effective in cleaning compounds otherwise difficult to remove from the tissues of the skin. Rather, efforts in the past have been directed to the combination of orange oil with other cleaning solvents to produce floor cleaners, glass cleaners and the like.

From the foregoing, it should be appreciated that the thrust of prior development of skin cleaners, other than soap, have been directed to petroleum based products and ammonia based products and the industry has ignored the potential for orange oil as a constituent of skin cleaning compounds. Despite the long felt need for better cleaners, the suitability of orange oil has thus not been recognized, and the inventors of the subject invention have found success by examining this substance contrary to the direction of inquiry adopted by the industry at large.

SUMMARY OF THE INVENTION

It is an object of the present invention to provide a new and useful compound for cleaning the human skin.

Another object of the present invention is to provide a skin cleaning compound suitable for cleaning non-water soluble products such as grease, caulking, adhesives, sealants, tar, oils, ink and the like.

Yet another object of the present invention is to provide a skin cleaning composition which is non-toxic.

It is a further object of the present invention is to provide a skin cleaning composition that is derived from natural vegetable and plant sources.

Still a further object of the present invention is to provide a skin cleaning composition that not only removes unwanted substances from the human skin but also acts to help clean and revitalize the human skin.

The present invention, then, provides a skin cleaning composition which is adapted for external use on human tissues. Broadly, this composition comprises a first ingredient being between five percent (5%) and sixty percent (60%) by volume of orange oil, a second ingredient being a pharmaceutically acceptable moisturizer for human skin and a third ingredient being an emulsifying agent. Preferably, the moisturizer is selected from a group consisting of: glycerin, aloe vera, jojoba oil, and safflower oil. Further, it is preferred that the emulsifying agent also function as an emollient. Preferably the emulsifying agent is a natural grain derivative, preferably either oat gum or oatmeal. Further, it is preferred that the first, second, and third ingredients are selected and mixed in a ratio such that the resulting skin cleaning composition has a pH range of between 4.5 and 6.0 inclusively. To this end, a fourth ingredient in the form of a buffering compound may be added to the composition.

In the more specific composition according to the preferred embodiment, the cleaning composition comprises forty-five percent (45%) or less by volume of orange oil, forty-five percent (45%) or less by volume of the emulsifying agent and the pharmaceutically acceptable moisturizer. The preferred emulsifying agent in this composition is oatmeal, and the preferred moisturizer is a mixture of jojoba oil, aloe vera and glycerin mixed by volume of approximately two parts jojoba oil, two parts aloe vera and one part glycerin. It is further desired to use a small portion of safflower oil both as a moisturizer and to help form a stable emulsion.

These and other objects of the present invention will become more readily appreciated and understood from a consideration of the following detailed description of the preferred embodiment:

DETAILED DESCRIPTION OF THE PREFERRED EMBODIMENT

The present invention is directed to a cleaning composition utilized on skin tissues and having, as its cleaning ingredient, the commercially available substance known as orange oil derived from the rinds of oranges. In this broad form, the composition includes orange oil, an emulsifying agent and a pharmaceutically acceptable moisturizer. In order to determine the preferred composition of the present invention, a series of samples having differing properties were evaluated to establish a desired range in pH and to establish the necessary proportion of orange oil to give suitable cleaning. These test samples are set forth below.

In their investigation of cleaning compositions according to the present invention, Applicants first investigated several compositions which were mixtures of orange oil, water, moisturizers and vitamin E. These samples were developed to test the cleaning properties of orange oil and to evaluate orange oil mixed with moisturizing agents. A test group of ten persons, male and female, were selected to subjectively evaluate the results of these samples. Initially, three such samples were prepared, and the compositions are set forth as Samples I-III, as follows:

SAMPLE I

| Ingredient | Volume Percent (Approximate) |
|---|---|
| Orange Oil | 39 |
| Water | 33 |
| Glycerin* | 12 |
| Aloe Vera* | 12 |
| Jojoba Oil* | 3 |
| Vitamin E | 1 |

*Total Moisturizers accounted for approximately 27% by volume.

SAMPLE II

| Ingredient | Volume Percent (Approximate) |
|---|---|
| Orange Oil | 34.5 |
| Water | 27.5 |
| Glycerin* | 17 |
| Aloe Vera* | 14 |
| Jojoba Oil* | 3.5 |
| Vitamin E | 3.5 |

*Total Moisturizers accounted for approximately 34.5% by volume.

SAMPLE III

| Ingredient | Volume Percent (Approximate) |
|---|---|
| Orange Oil | 37 |
| Water | 26 |
| Glycerin* | 14.75 |
| Aloe Vera* | 14.75 |
| Jojoba Oil* | 3.5 |
| Vitamin E | 4 |

*Total Moisturizers accounted for approximately 33% by volume.

Prior to presenting these samples to the test group, Applicants tested the relative acidity of the samples since it was believed desirable to avoid a composition that was either too acidic or too basic. The result of this acidity measurement, correlated to the Samples, is set forth in Table 1 below:

TABLE 1

| Sample | pH (Approximate) |
|---|---|
| I | 4.5 |
| II | 5 |
| III | 4.7 |

In each of the cases of Samples I-III, the respective components were mixed and blended in an attempt to form an emulsion. An initial problem was noted with each of these Samples, however, in that the emulsion separated, that is, "broke" after approximately one to two days. Since it was fairly simple to re-blend the Samples, Samples I-III were submitted to the test group for evaluation. Generally, the results of the composition was excellent with each of Samples I-III readily removing polyurethane and silicone base caulking compounds, tars, grease, oil and adhesives; each of these industrial type substances are regarded as difficult to remove, from the human hands. All ten members of the test group reported comparable cleaning properties and reported that their hands were left soft after a two week period of using the compounds. Indeed, after two weeks of use, certain male members of the test group who had dry hands resulting from the use of other solvents noted substantial improvement in the texture and softness of their hands. No allergic reactions were reported by any members of the test group.

After determining that test Samples I-III performed adequately in cleaning the hands and in moisturizing the hands, it became necessary to determine whether the oil orange and moisturizer emulsion could be stabilized so that it would not break over a period of time. In order to determine if a natural ingredient could act as an emulsifying agent, the Applicants selected a grain base derivative as an emulsifying agent. To this end, Applicants tested oatmeal gum and oatmeal to act as the primary emulsifier. Accordingly, two more test samples, Samples IV and V were prepared according to the compositions set forth below:

SAMPLE IV

| Ingredient | Volume Percent (Approximate) |
|---|---|
| Orange Oil | 42.75 |
| Aloe Vera* | 7 |
| Jojoba Oil* | 3.5 |
| Safflower Oil* | 4 |
| Oatmeal Gum | 42.75 |

*Total Moisturizers accounted for approximately 14.5% by volume.

SAMPLE V

| Ingredient | Volume Percent (Approximate) |
|---|---|
| Orange Oil | 36.5 |
| Aloe Vera | 14 |
| Jojoba Oil* | 14 |
| Glycerin* | 7 |
| Safflower Oil* | 0.5 |
| Oatmeal | 28 |

*Total Moisturizers accounted for approximately 35.5% by volume.

It may be noted that, in Samples IV and V, vitamin E and water were both omitted from the composition. However, it should be noted that both the oatmeal gum in Sample IV and the oatmeal in Sample V each contain a portion of water. In Sample IV, the oatmeal gum was prepared by boiling rolled oats in water and straining the resultant mass to remove the hulls. In Sample V, rolled oats were boiled in water and the resulting mass (containing approximately 50% water) was used to prepare the composition. Relatively equal parts of orange oil and oat derivatives were used and a small portion of safflower oil was included. Again, relative acidity was tested and it was found that Sample IV had a pH of approximately 5.0 while Sample V had a pH of 5.5.

Samples IV and V were submitted to the test group to evaluate cleaning effectiveness and moisturizing ability. Further, observation of the two compositions were made to determine whether or not the emulsions broke. The results of this study determined that the emulsion of Sample IV broke after approximately seven days while the emulsion according to Sample V did not separate over any observed duration of time (several months). The test group observed that the cleaning properties of Samples IV and V were almost, but not quite, as effective as the cleaning properties of Samples I-III, but that the cleaning effectiveness was estimated at approximately 90% of Samples I-III. With respect to Sample IV, the test group reported that their hands did not roughen, but that the sample did not feel as comfortable when on the hands. With respect to Sample V, the test group reported that the emulsion both felt comfortable on the hands and left their hands soft after approximately five days of regular usage. In each case, the emulsions were able to clean all caulking materials and tars, including silicone and polyurethane based caulking compounds as well as oil and grease from the skin. Further tests were conducted on compositions similar to Sample V were in the amount of orange oil was slightly increased while holding the amounts of the remaining ingredients constant until the emulsion broke. It was found that, with these compositions, the emulsion broke when orange oil accounted for approximately 38% by volume of the composition.

From the foregoing, Applicants determined that Sample V offered the best compromise among emulsion stability, cleaning effectiveness, and skin effect. Therefore, utilizing Sample V as a reference, Applicants adjusted the amount of orange oil (ignoring whether the emulsion broke) to determine an effective pH range wherein the composition felt comfortable on the human hands. A first set of samples set forth below as Samples VI-IX were prepared to be less acidic than Sample V, and a second set of test samples, set forth below as Samples X-XIII were tested for compositions having greater acidity than Sample V. Samples VI-IX were prepared by simply buffering Sample V with differing amounts of sodium bicarbonate. The resulting samples were buffered to have pH values according to Table 2 as follows:

TABLE 2

| Sample | pH (Approximate) |
| --- | --- |
| VI | 9.0 |
| VII | 8.0 |
| VIII | 7.0 |
| IX | 6.0 |

Each of Samples VI-IX were evaluated by the test group. Samples VI and VII were reported to immediately make the hands dry upon first application of the respective composition and removal of the composition with water. With respect to Samples VIII and IX, the test group reported less drying than Samples VI and VII although more dryness of the hands was noted in comparison to test Sample V. These empirical observations lead Applicants to conclude that an acidity of at least ph 6.0 is desirable, that is, that the preferred composition should not be more basic than ph 6.0.

To evaluate test compositions for excess acidity, Applicants merely increased the amount of orange oil in test Sample V while holding the amounts of the remaining ingredients constant to obtain desired acidity levels according to Table 3, below:

TABLE 3

| Sample | pH (Approximately) |
| --- | --- |
| X | 2.5 |
| XI | 3.0 |
| XII | 3.5 |
| XIII | 4.0 |

Test Sample X had a volume percent of approximately 80% orange oil, Sample IX had orange oil of approximately 70% by volume, Sample XII had orange oil of approximately 60% by volume, and Sample XIII had orange oil of approximately 50% by volume.

It had previously been found that orange oil alone exhibited excellent cleaning properties, but left the hands feeling too dry and too astringent. With respect to Samples X-XIII, in each case no emulsion formed. The test group reported that each of Samples X-XIII had excellent cleaning properties, but the emulsions felt too astringent on the hands even after limited use. Applicants accordingly concluded that it was desirable that the emulsified composition have a pH that is approximately 4.5. Thus, Applicants further concluded that the composition according to the preferred embodiment of the present invention should have a pH of between 4.5 and 6.0, inclusively.

As noted in the above examples, the emulsions according to Sample V broke at approximately 38% orange oil by volume. In order to evaluate cleaning properties as a function of percent volume of orange oil, additional samples were prepared wherein the weight percentages of the ingredients other than orange oil was held constant while the amount of orange oil was varied to provide differing volume percentages of orange oil. Accordingly, Samples XIV-XVII were prepared to have volume percents of orange oil approximately 5%, 10%, 15% and 25%, respectively. In each case, the emulsions were stable. These Samples XIV-XVII were given to the test group to subjectively evaluate cleaning effectiveness. With respect to Sample XIV, the test group reported that cleaning properties were substantially reduced; Sample XIV could not effectively clean tar or caulking compounds. Indeed, Sample XIV was only effective in removing cosmetics from the skin. Sample XV eventually was able to remove silicone caulking compounds but was unable to remove polyurethane caulkings or tar. With respect to Sample XVI, the test group reported about 50%-60% of the cleaning effectiveness of Sample V with no marked increase in benefits in skin softening. Sample XVII was reported to have approximately 80% of the cleaning effectiveness of Sample V in removing all of the tested materials, but again there was no report of skin enhancements over Sample V.

From these tests, Applicants concluded that, with respect to cosmetics, a composition according to the present invention could have as little as 5% by volume of orange oil although it was preferable to have a cleaning composition having at least 25% by volume of orange oil.

To determine whether the moisturizers had any effect on the composition or whether pH was the dominant skin effecting property, Applicants prepared yet another sample, Sample XVIII, wherein 100% orange oil was buffered with sodium bicarbonate so that it had a pH of 5.5. This Sample XVIII was tested and it was determined that it was exceptionally drying and astringent on the human hands. Indeed, Sample XVIII proved almost as drying and astringent as Sample X.

In order to increase the amount of orange oil, Applicants further tested a variation on Sample V wherein both the amount of orange oil and the amount of oatmeal were increased while the amount of moisturizers was decreased. This Sample XIX, was prepared as follows:

SAMPLE XIX

| Ingredient | Volume Percent (Approximate) |
| --- | --- |
| Orange Oil | 40.5 |
| Aloe Vera* | 7.75 |
| Jojoba Oil* | 7.75 |
| Glycerin* | 4.5 |
| Safflower Oil* | .5 |
| Oatmeal | 39 |

*Total Moisturizers accounted for 20.5% by volume.

From Sample XIX, it was concluded that orange oil could be increased, along with a corresponding increase in an oat grain derivative, until approximately 45% by volume of orange oil was included in the composition. Any amount of orange oil in excess of this amount would result in the diminishment of moisturizers so as to negate the softening effect of the hand cleaning composition according to the preferred invention.

Other samples, set forth below as Samples XX-XXIII were prepared utilizing other materials. These samples are as follows:

SAMPLE XX

| Ingredient | Volume Percent (Approximate) |
| --- | --- |
| Orange Oil | 50 |
| Olive Oil | 25 |
| Jojoba Oil | 25 |
| Baking Soda | Trace |

SAMPLE XXI

| Ingredient | Volume Percent (Approximate) |
| --- | --- |
| Orange Oil | 50 |
| Glycerin | 50 |

SAMPLE XXII

| Ingredient | Volume Percent (Approximate) |
| --- | --- |
| Orange Oil | 50 |
| Aloe Vera | 50 |

SAMPLE XXIII

| Ingredient | Volume Percent (Approximate) |
| --- | --- |
| Orange Oil | 12.5 |
| Vitamin E | 87.5 |

Sample XX was found to have a pH of approximately 8.5. While Sample XX was deemed effective in cleaning, there was some reduction of cleaning effectiveness over Sample V and the composition left a dryness when wiped off of the skin. Further, the emulsion broke almost immediately. With respect to Samples XXI and XXII, both samples left a sticky residue on the hands but were approximately equal in cleaning effectiveness to Sample V. Sample XXI had a pH a little greater than 2.0 while Sample XXII had a pH of approximately 3.5.

It was thus observed that aloe vera had some buffering effect on the acidity of the orange oil. Each of Samples XXI and XXII were highly astringent and left the test groups hands dry after washing with water. With respect to Sample XXIII, again this sample proved effective in removing cosmetics, but the sample was not effect in removing heavier, industrial substances such as caulking compounds, adhesives, tars and the like. The orange oil and Vitamin E, however, did mix without separation and a resulting acidity of pH 5.0.

From the information derived form all of the aforementioned samples, Applicants determined that glycerin and safflower oil are both desirable in the preferred compositions. On one hand glycerin appears both to stabilize the emulsion and perform as a moisturizer while, on the other hand, safflower oil appears to act as an emulsion stabilizer, as an emulsifying agent and as a moisturizer.

According to the above, Applicants prefer the compositions set forth in Sample V and Sample XIX for use in cleaning unwanted materials from human skin. In order to test administration of the preferred composition, Applicants applied the compound directly to the skin as a liquid emulsion and removed the emulsion from the hands by washing with water. In addition, Applicants were successful in soaking towellets, formed of standard absorbent material such as paper, cloth and the like, in the liquid emulsion so that a towellet would become impregnated with the cleaning composition. These towellets can be hermetically sealed in standard foil packages, as known in the industry, so that the user can simply remove from the skin any of the described unwanted materials with a pre-moistened towellet. This is particularly useful in situations where water is not readily available. Further, individualized packets of pre-moistened towellets are convenient for portability and on-the-job use.

From the foregoing, the inventors have concluded that a suitable skin cleaning composition can be prepared wherein the skin composition has a first ingredient of between 5% and 60% by volume of orange oil, a second ingredient being a pharmaceutical acceptable moisturizer for human skin and a third ingredient being an emulsifying agent. Preferably, the moisturizer is either one or more of a group of moisturizes selected from the following: glycerin, aloe vera, jojoba oil, safflower oil. However, other pharmaceutically acceptable moisturizers are within the scope of this invention as could be developed without undue experimentation by the ordinarily skilled chemist according to the teachings of the present invention. One example of such a moisturizer is glycerin stearate. These other compositions are thus intended, unless otherwise specifically limited, to be encompassed by the general phrase "moisturizer" both in this specification and in the appended claims. In any event, it is preferred that the resultant composition have a pH between 4.5 to 6.0 and can be so buffered if necessary by the utilization of aloe vera or a buffering agent, such as baking soda.

Accordingly, the present invention has been described with some degree of particularity directed to the preferred embodiment of the present invention. It should be appreciated, though, that the present invention is defined by the following claims construed in light of the prior art so that modifications or changes may be made to the preferred embodiment of the present invention without departing from the inventive concepts contained herein.

We claim:

1. A skin cleaning composition adapted for external use on human tissues, comprising a first ingredient being between five percent (5%) and sixty percent (60%) by volume of orange oil, a second ingredient being a pharmaceutically acceptable moisturizer for human skin and a third ingredient being an emulsifying agent in the form of an oat grain derivative product.

2. A skin cleaning composition according to claim 1 wherein said moisturizer is selected from a group consisting of: glycerin, aloe vera, jojoba oil, and safflower oil.

3. A skin cleaning composition according to claim 1 wherein said oat grain derivative product is one of oat gum and oatmeal.

4. A skin cleaning composition according to claim 1 wherein said first, second and third ingredients are selected and mixed in a ratio such that the resulting skin cleaning composition has a pH range of between 4.5 to 6.0, inclusively.

5. A skin cleaning composition according to claim 1 including as a fourth ingredient a buffering compound in a proportion such that the resulting composition is pH balanced within a range of 4.5 to 6.0, inclusively.

6. A skin cleaning composition for external use on human tissues, comprising orange oil, a pharmaceutically acceptable moisturizer for human skin and an oat grain derivative product as an emulsifying agent, wherein said composition has a pH within a range of 4.5 to 6.0, inclusively.

7. A skin cleaning composition according to claim 5 including a buffering compound.

8. A skin cleaning composition according to claim 5 wherein said moisturizer is selected from a group consisting of: glycerin, aloe vera, jojoba oil, safflower oil and glycerol stearate.

9. A cleaning composition for use on human skin comprising forty-five percent (45%) or less by volume of orange oil, forty-five percent (45%) or less by volume of oatmeal and a pharmaceutically acceptable moisturizer.

10. A cleaning composition according to claim 8 wherein said moisturizer is a mixture of jojoba oil, aloe vera and glycerin.

11. A cleaning composition according to claim 1 wherein said mixture includes by volume two parts jojoba oil, two parts aloe vera and one part glycerin.

12. A cleaning composition according to claim 9 wherein said mixture includes safflower oil.

* * * * *